(12) United States Patent
Kesler et al.

(10) Patent No.: US 9,418,496 B2
(45) Date of Patent: Aug. 16, 2016

(54) AUTOMATED POSTFLIGHT TROUBLESHOOTING

(75) Inventors: Paul Allen Kesler, Arlington, VA (US); Robert Daniel Kalinowski, Saint Charles, MO (US); John Lyle Vian, Renton, WA (US)

(73) Assignee: THE BOEING COMPANY, Chicago, IL (US)

( * ) Notice: Subject to any disclaimer, the term of this patent is extended or adjusted under 35 U.S.C. 154(b) by 117 days.

(21) Appl. No.: 12/372,616

(22) Filed: Feb. 17, 2009

(65) Prior Publication Data

US 2010/0211358 A1    Aug. 19, 2010

(51) Int. Cl.
| | | |
|---|---|---|
| G21C 17/00 | (2006.01) | |
| G07C 9/00 | (2006.01) | |
| G01N 21/00 | (2006.01) | |
| G07C 5/00 | (2006.01) | |
| G01N 21/88 | (2006.01) | |
| G01N 21/01 | (2006.01) | |

(52) U.S. Cl.
CPC ............ *G07C 9/00111* (2013.01); *G01N 21/00* (2013.01); *G01N 21/01* (2013.01); *G01N 21/8851* (2013.01); *G07C 5/006* (2013.01); *G01N 21/88* (2013.01); *G01N 2291/106* (2013.01); *G01N 2291/26* (2013.01)

(58) Field of Classification Search
CPC .. G07C 9/00111; G07C 5/006; G07C 5/0808; G07C 5/0816; G01N 21/88; G01N 2291/26; G01N 2291/2623; G01N 2291/2696; G01N 2291/106; G01N 21/8851; G06K 2017/0077; G06K 9/00214; G01M 5/0016; G01M 5/0033
See application file for complete search history.

(56) References Cited

U.S. PATENT DOCUMENTS

| | | | |
|---|---|---|---|
| 2,849,701 A | | 8/1958 | Clark |
| 4,463,428 A | | 7/1984 | Gilliam |
| 4,827,416 A | | 5/1989 | Kawagoe et al. |
| 4,897,551 A | * | 1/1990 | Gersh et al. ................. 250/461.1 |
| 4,918,321 A | | 4/1990 | Klenk et al. |
| 5,014,042 A | | 5/1991 | Michoud et al. |
| 5,036,935 A | | 8/1991 | Kohara |
| 5,203,646 A | | 4/1993 | Landsberger et al. |

(Continued)

FOREIGN PATENT DOCUMENTS

| | | |
|---|---|---|
| EP | 0512866 A1 | 11/1992 |
| EP | 1193168 A2 | 4/2002 |

(Continued)

OTHER PUBLICATIONS

U.S. Appl. No. 11/857,217, filed Sep. 18, 2007, Vian et al.

(Continued)

*Primary Examiner* — Sujoy Kundu
*Assistant Examiner* — L. Anderson
(74) *Attorney, Agent, or Firm* — Yee & Associates, P.C.

(57) ABSTRACT

The advantageous embodiments provide a method for identifying anomalies on an object. The advantageous embodiments detect a presence of the object in a control area using a sensor system. In response to detecting the presence of the object in the control area, the object is identified using the sensor system. Scan priorities are identified for the object using the sensor system. The object is scanned while the object is within the control area to form scan results. The scan results are analyzed and a determination is made as to whether a number of maintenance anomalies are detected on the object using the scan results.

12 Claims, 6 Drawing Sheets

(56) References Cited

U.S. PATENT DOCUMENTS

| | | | |
|---|---|---|---|
| 5,220,263 A | 6/1993 | Onishi et al. | |
| 5,237,404 A | 8/1993 | Tanaka et al. | |
| 5,318,254 A | 6/1994 | Shaw et al. | |
| 5,324,948 A | 6/1994 | Dudar et al. | |
| 5,334,982 A | 8/1994 | Owen | |
| 5,340,056 A | 8/1994 | Guelman et al. | |
| 5,351,621 A | 10/1994 | Tanaka et al. | |
| 5,416,476 A | 5/1995 | Rendon | |
| 5,487,440 A | 1/1996 | Seemann | |
| 5,490,646 A | 2/1996 | Shaw et al. | |
| 5,586,028 A | 12/1996 | Sekine et al. | |
| 5,633,707 A | 5/1997 | Seemann | |
| 5,695,155 A | 12/1997 | Macdonald et al. | |
| 5,726,705 A | 3/1998 | Imanishi et al. | |
| 5,831,570 A | 11/1998 | Ammar et al. | |
| 5,832,187 A | 11/1998 | Pedersen et al. | |
| 5,845,002 A | 12/1998 | Heck et al. | |
| 5,845,725 A | 12/1998 | Kawada | |
| 5,982,278 A | 11/1999 | Cuvelier | |
| 5,995,884 A | 11/1999 | Allen et al. | |
| 6,236,735 B1 | 5/2001 | Bjorner et al. | |
| 6,266,138 B1 | 7/2001 | Keshavmurthy | |
| 6,293,141 B1 | 9/2001 | Nance | |
| 6,364,026 B1 | 4/2002 | Doshay | |
| 6,476,712 B1 | 11/2002 | Achterholt | |
| 6,565,361 B2 | 5/2003 | Jones et al. | |
| 6,606,563 B2 | 8/2003 | Corcoran, III | |
| 6,671,588 B2 | 12/2003 | Otake et al. | |
| 6,819,265 B2 | 11/2004 | Jamieson et al. | |
| 6,825,758 B1 | 11/2004 | Laitsaari | |
| 6,842,674 B2 | 1/2005 | Solomon | |
| 6,888,446 B2 | 5/2005 | Nantz et al. | |
| 6,898,484 B2 | 5/2005 | Lemelson et al. | |
| 6,904,335 B2 | 6/2005 | Solomon | |
| 6,907,799 B2 | 6/2005 | Jacobsen et al. | |
| 6,947,797 B2 * | 9/2005 | Dean et al. | 700/79 |
| 6,953,094 B2 | 10/2005 | Ross et al. | |
| 6,970,576 B1 | 11/2005 | Tilsley | |
| 6,984,952 B2 | 1/2006 | Peless et al. | |
| 7,076,335 B2 | 7/2006 | Seemann | |
| 7,212,106 B2 | 5/2007 | Katou | |
| 7,218,993 B2 | 5/2007 | Yasukawa et al. | |
| 7,236,861 B2 | 6/2007 | Paradis et al. | |
| 7,250,849 B2 | 7/2007 | Spriggs et al. | |
| 7,280,890 B2 | 10/2007 | Seemann | |
| 7,303,010 B2 | 12/2007 | de Guzman et al. | |
| 7,327,112 B1 | 2/2008 | Hlynka et al. | |
| 7,337,156 B2 | 2/2008 | Wippich | |
| 7,343,222 B2 | 3/2008 | Solomon | |
| 7,414,523 B2 | 8/2008 | Li et al. | |
| 7,417,738 B2 | 8/2008 | Taylor et al. | |
| 7,499,772 B2 | 3/2009 | Wilcox et al. | |
| 7,501,616 B2 | 3/2009 | Wiklof | |
| 7,586,422 B2 | 9/2009 | Goodman et al. | |
| 7,626,513 B2 | 12/2009 | Goodman et al. | |
| 7,627,447 B2 | 12/2009 | Marsh et al. | |
| 7,714,702 B2 | 5/2010 | Khuzadi | |
| 7,765,038 B2 | 7/2010 | Appleby et al. | |
| 7,765,668 B2 | 8/2010 | Townsend et al. | |
| 7,796,018 B2 | 9/2010 | Khuzadi | |
| 7,797,095 B2 | 9/2010 | Rado | |
| 7,813,888 B2 | 10/2010 | Vian et al. | |
| 7,817,026 B2 | 10/2010 | Watabe et al. | |
| 7,832,281 B2 | 11/2010 | Mian et al. | |
| 7,844,364 B2 | 11/2010 | McLurkin et al. | |
| 7,860,618 B2 | 12/2010 | Brandstetter et al. | |
| 7,894,948 B2 | 2/2011 | Stroud | |
| 7,896,113 B1 | 3/2011 | Ramirez | |
| 7,941,261 B2 | 5/2011 | Johnsen | |
| 8,051,547 B2 | 11/2011 | Toh et al. | |
| 8,060,270 B2 | 11/2011 | Vian et al. | |
| 8,078,319 B2 | 12/2011 | Franke et al. | |
| 8,140,250 B2 | 3/2012 | Mian et al. | |
| 8,145,367 B2 | 3/2012 | Khatwa et al. | |
| 8,150,105 B2 | 4/2012 | Mian et al. | |
| 8,181,532 B2 | 5/2012 | Schmidt et al. | |
| 8,260,485 B1 | 9/2012 | Meuth et al. | |
| 8,504,505 B2 | 8/2013 | Mintah | |
| 8,874,305 B2 | 10/2014 | Dolgov et al. | |
| 2002/0073788 A1 | 6/2002 | Hatley et al. | |
| 2002/0082769 A1 * | 6/2002 | Church et al. | 701/120 |
| 2003/0048106 A1 | 3/2003 | Seemann | |
| 2003/0089183 A1 | 5/2003 | Jacobsen et al. | |
| 2003/0135327 A1 | 7/2003 | Levine et al. | |
| 2003/0169335 A1 | 9/2003 | Monroe | |
| 2004/0030571 A1 | 2/2004 | Solomon | |
| 2004/0054507 A1 | 3/2004 | Mott | |
| 2004/0055746 A1 | 3/2004 | Ross et al. | |
| 2004/0073324 A1 * | 4/2004 | Pierro et al. | 700/90 |
| 2004/0073411 A1 | 4/2004 | Alston et al. | |
| 2004/0158358 A1 | 8/2004 | Anezaki et al. | |
| 2005/0033517 A1 | 2/2005 | Kondoh et al. | |
| 2005/0073585 A1 | 4/2005 | Ettinger et al. | |
| 2005/0113943 A1 | 5/2005 | Nian | |
| 2005/0113975 A1 | 5/2005 | Seemann | |
| 2005/0126794 A1 | 6/2005 | Palmer et al. | |
| 2005/0217589 A1 | 10/2005 | Daniel et al. | |
| 2005/0251291 A1 | 11/2005 | Solomon | |
| 2005/0258943 A1 * | 11/2005 | Mian et al. | 340/426.1 |
| 2006/0085106 A1 | 4/2006 | Gaudiano et al. | |
| 2006/0114531 A1 | 6/2006 | Webb et al. | |
| 2006/0184291 A1 | 8/2006 | Paradis et al. | |
| 2006/0198952 A1 | 9/2006 | Nagase et al. | |
| 2006/0242820 A1 * | 11/2006 | Townsend et al. | 29/703 |
| 2006/0243857 A1 | 11/2006 | Rado | |
| 2006/0271251 A1 | 11/2006 | Hopkins | |
| 2007/0062299 A1 | 3/2007 | Mian et al. | |
| 2007/0081154 A1 | 4/2007 | Mapoles et al. | |
| 2007/0113690 A1 | 5/2007 | Wilcox et al. | |
| 2007/0129847 A1 | 6/2007 | Ulmer et al. | |
| 2007/0146728 A1 | 6/2007 | Pristner | |
| 2007/0208442 A1 | 9/2007 | Perrone | |
| 2007/0272841 A1 | 11/2007 | Wiklof | |
| 2008/0004749 A1 | 1/2008 | Hostettler | |
| 2008/0021604 A1 | 1/2008 | Bouvier et al. | |
| 2008/0140318 A1 | 6/2008 | Breed | |
| 2008/0148876 A1 | 6/2008 | Hock et al. | |
| 2008/0154458 A1 | 6/2008 | Brandstetter et al. | |
| 2008/0177411 A1 | 7/2008 | Marsh et al. | |
| 2008/0252489 A1 | 10/2008 | Naimer et al. | |
| 2008/0270866 A1 | 10/2008 | Choi et al. | |
| 2008/0297333 A1 | 12/2008 | Khuzadi | |
| 2008/0297375 A1 | 12/2008 | Khuzadi | |
| 2009/0055043 A1 * | 2/2009 | Mian et al. | 701/29 |
| 2009/0079839 A1 | 3/2009 | Fischer et al. | |
| 2009/0219393 A1 | 9/2009 | Vian et al. | |
| 2009/0243828 A1 | 10/2009 | Hering et al. | |
| 2009/0285491 A1 | 11/2009 | Ravenscroft et al. | |
| 2009/0290757 A1 * | 11/2009 | Mian et al. | 382/104 |
| 2010/0017052 A1 | 1/2010 | Luce | |
| 2010/0023201 A1 | 1/2010 | Kinney et al. | |
| 2010/0039294 A1 | 2/2010 | Feyereisen et al. | |
| 2010/0063650 A1 | 3/2010 | Vian et al. | |
| 2010/0094487 A1 | 4/2010 | Brinkman | |
| 2010/0235037 A1 | 9/2010 | Vian et al. | |
| 2010/0250022 A1 | 9/2010 | Hines et al. | |
| 2010/0271191 A1 | 10/2010 | de Graff et al. | |
| 2010/0312387 A1 | 12/2010 | Jang et al. | |
| 2010/0312388 A1 | 12/2010 | Jang et al. | |
| 2011/0313614 A1 | 12/2011 | Hinnant, Jr. et al. | |
| 2012/0038492 A1 | 2/2012 | Maggiore et al. | |
| 2012/0041639 A1 | 2/2012 | Followell et al. | |
| 2012/0081540 A1 | 4/2012 | Jang | |
| 2012/0130701 A1 | 5/2012 | Khella | |
| 2013/0261876 A1 | 10/2013 | Froom et al. | |
| 2014/0222325 A1 | 8/2014 | Followell et al. | |

FOREIGN PATENT DOCUMENTS

| | | |
|---|---|---|
| EP | 1619625 | 1/2006 |
| EP | 1884453 A2 | 2/2008 |
| EP | 2208971 | 7/2010 |
| EP | 2259245 | 12/2010 |
| FR | 2930669 A1 | 10/2009 |

(56) References Cited

FOREIGN PATENT DOCUMENTS

| GB | 2308656 | | 7/1997 |
|---|---|---|---|
| GB | 2429819 | | 3/2007 |
| JP | 2007183172 | A | 7/2007 |
| WO | WO2004081488 | | 9/2004 |
| WO | WO2005113261 | | 12/2005 |
| WO | WO2006053433 | | 5/2006 |
| WO | WO2007080584 | | 7/2007 |
| WO | 2008127468 | A2 | 10/2008 |
| WO | 2009142933 | A2 | 11/2009 |
| WO | WO2010141180 | | 12/2010 |
| WO | WO2011119634 | | 9/2011 |
| WO | WO2012021177 | | 2/2012 |
| WO | WO2012021179 | | 2/2012 |
| WO | WO2012047479 | | 4/2012 |

OTHER PUBLICATIONS

U.S. Appl. No. 12/124,511, filed May 21, 2008, Vian et al.
U.S. Appl. No. 12/205,658, filed Sep. 5, 2008, Vian et al.
U.S. Appl. No. 12/124,565, filed May 21, 2008, Vian et al.
U.S. Appl. No. 12/479,667, filed Jun. 5, 2009, Jang et al.
U.S. Appl. No. 12/560,569, filed Feb. 5, 2010, Jang et al.
U.S. Appl. No. 12/701,033, filed Feb. 5, 2010, Kesler et al.
U.S. Appl. No. 12/404,493, filed Mar. 16, 2009, Vian et al.
International Search Report for Application No. PCT/US2010/033917 dated Nov. 26, 2010.
PCT Search Report regarding Application PCT/US2011/029466, filing date Mar. 22, 2011, Issued by International Searching Authority.
GB Combined Search and Examination Report for application P49034GB/AER dated Jun. 10, 2010.
"In-Sight Line Scan Vision System", Cognex, Webinar, retrieved Feb. 5, 2010, 17 pages.
Ollero, "Mutliple Heterogenous Unmanned Aerial Vehicles", Springer Tracts in Advanced Robotics, vol. 37, Copyright 2007, 233 pages (Abstract).
"Unmanned Aerial Vehicle (UAV) ZALA 421-04M chosen for Aerial Monitoring of Forest Fires", published by news.wood.ru, Feb. 2010, 3 pages.
Frost, "A Practical Guide to Using the In-Sight 5604 Line Scan Vision System", Cognex, In-Sight Vision Systems, Mar. 2009, 20 pages.
Gunatilake et al., "Image Understanding Algorithms for Remote Visual Inspection of Aircraft Surfaces", Proceedings of the SPIE conference on Machine Vision Applications in Industrial Inspection V, Copyright 1997, 12 pages.
DeVault, "Robotic system for underwater inspection of bridge piers", IEEE Instrumentation & Measurement Magazine, vol. 3, Iss.3, Sep. 2000, pp. 32-37 (Abstract).
PCT Search Report and Written Opinion dated Jun. 8, 2011 regarding international application PCT/US2011/029766, applicant's reference 10-0173PCT, applicant The Boeing Company, 9 pages.
PCT Search Report dated Feb. 16, 2012 regarding international application PCT/US2011/030150, applicant's reference 10-0174PCT, applicant The Boeing Company, 6 pages.
PCT Search Report dated Feb. 7, 2012 regarding international application PCT/US2011/051830, applicant's reference 10-0602PCT, applicant The Boeing Company, 4 pages.
USPTO Office Action dated Oct. 4, 2011 regarding U.S. Appl. No. 12/701,033, 24 pages.
Response to Office Action dated Jan. 4, 2012 regarding U.S. Appl. No. 12/701,033, 12 pages.
USPTO Final Office Action dated Apr. 13, 2012 regarding U.S. Appl. No. 12/701,033, 18 pages.
USPTO Office Action dated Apr. 13, 2012 regarding U.S. Appl. No. 12/404,493, 22 pages.
USPTO Office Action dated Jun. 15, 2012 regarding U.S. Appl. No. 13/086,521, 18 pages.
USPTO Office Action dated Nov. 8, 2010 regarding U.S. Appl. No. 12/124,565, 13 pages.
USPTO Final Office Action dated Mar. 15, 2011 regarding U.S. Appl. No. 12/124,565, 14 pages.
USPTO Notice of Allowance dated Aug. 18, 2011 regarding U.S. Appl. No. 12/124,565, 7 pages.
USPTO Office Action dated Feb. 24, 2012 regarding U.S. Appl. No. 12/560,569, 27 pages.
USPTO Final Office Action dated Jul. 24, 2012 regarding U.S. Appl. No. 12/560,569, 23 pages.
USPTO Office Action dated Feb. 21, 2012 regarding U.S. Appl. No. 12/479,667, 25 pages.
Maggiore et al., "Runway Condition Monitoring", U.S. Appl. No. 12/730,594, filed Mar. 14, 2010, 43 pages.
Vian et al., "Fire Management System", U.S. Appl. No. 13/086,521, filed Apr. 14, 2011, 56 pages.
UK Intellectual Property Office Combined Search and Examination Report, dated Jun. 10, 2010, regarding Application No. GB1003830.5, 8 pages.
Office Action, dated Aug. 31, 2012, regarding U.S. Appl. No. 12/701,033, 28 pages.
Amendment Pursuant to Request for Continued Examination, dated Aug. 13, 2012, regarding U.S. Appl. No. 12/701,033, 15 pages.
Office Action, dated Aug. 16, 2012, regarding U.S. Appl. No. 12/730,594, 25 pages.
Final Office Action, dated Oct. 3, 2012, regarding U.S. Appl. No. 12/404,493. 18 pages.
Office Action, dated Aug. 31, 2012, regarding U.S. Appl. No. 12/854,646, 19 pages.
Office Action, dated May 23, 2013, regarding U.S. Appl. No. 12/70,594, 28 pages.
Final Office Action, dated Mar. 7, 2013, regarding U.S. Appl. No. 12/854,646, 22 pages.
Office Action, dated Mar. 28, 2013, regarding U.S. Appl. No. 12/854,671, 37 pages.
GB Search Report and Examination Report dated Jun. 15, 2011 regarding application GB1100763.0, applicant's reference P51280GB/AER/LJW, applicant The Boeing Company, 7 pages.
Final Office Action, dated Jan. 8, 2013, regarding U.S. Appl. No. 12/701,033, 27 pages.
Final Office Action, dated Dec. 20, 2012, regarding U.S. Appl. No. 12/730,594, 35 pages.
Office Action, dated Dec. 6, 2012, regarding U.S. Appl. No. 12/897,158, 51 pages.
Office Action, dated Sep. 12, 2013, regarding U.S. Appl. No. 12/701,033, 25 pages.
Office Action, dated Jul. 18, 2013, regarding U.S. Appl. No. 12/404,493, 42 pages.
Office Action, dated Aug. 28, 2013, regarding U.S. Appl. No. 12/560,569, 46 pages.
Notice of Allowance, dated Jul. 31, 2013, regarding U.S. Appl. No. 12/854,646, 19 pages.
Final Office Action, dated Jul. 12, 2013, regarding U.S. Appl. No. 12/854,671, 17 pages.
Final Office Action, dated Jun. 26, 2013, regarding U.S. Appl. No. 12/897,158 38 pages.
European Patent Office Communication, dated Jul. 23, 2013, regarding Application No. EP11713911.3, 6 pages.
Final Office Action, dated Oct. 10, 2013, regarding U.S. Appl. No. 12/730,594, 33 pages.
Final Office Action, dated Dec. 13, 2013, regarding U.S. Appl. No. 12/404,493, 24 pages.
Notice of Allowance, dated Dec. 13, 2013, regarding U.S. Appl. No. 12/854,671, 12 pages.
Notice of Allowance, dated Apr. 9, 2014, regarding U.S. Appl. No. 12/404,493, 20 pages.
Final Office Action, dated Feb. 21, 2014, regarding U.S. Appl. No. 12/701,033, 31 pages.
Final Office Action, dated Feb. 28, 2014, regarding U.S. Appl. No. 12/560,569, 43 pages.
Notice of Allowance, dated Feb. 27, 2014, regarding U.S. Appl. No. 12/730,594, 11 pages.
Office Action, dated Apr. 8, 2014, regarding U.S. Appl. No. 12/897,158, 33 pages.
Final Office Action, dated Feb. 19, 2014, regarding U.S. Appl. No. 13/086,521, 18 pages.

(56) References Cited

OTHER PUBLICATIONS

Office Action, dated Sep. 16, 2014, regarding U.S. Appl. No. 12/560,569, 46 pages.
Final Office Action, dated Sep. 8, 2014, regarding U.S. Appl. No. 12/897,158, 36 pages.
Notice of Allowance, dated Oct. 28, 2014, regarding U.S. Appl. No. 12/897,158, 12 pages.
Office Action, dated Aug. 8, 2014, regarding U.S. Appl. No. 13/086,521, 20 pages.
Final Office Action, dated Jan. 14, 2015, regarding U.S. Appl. No. 13/086,521, 23 pages.
Final Office Action, dated Dec. 29, 2014, regarding U.S. Appl. No. 12/560,569, 17 pages.
Office Action, dated Apr. 15, 2015, regarding U.S. Appl. No. 12/701,033, 37 pages.
Notice of allowance, dated Jan. 28, 2015, regarding U.S. Appl. No. 12/560,569, 6 pages.
Office Action, dated Oct. 7, 2015, regarding U.S. Appl. No. 14/246,143, 55 pages.
Office Action, dated Mar. 24, 2016, regarding U.S. Appl. No. 12/701,033, 38 pages.
Final Office Action, dated Feb. 23, 2016, regarding U.S. Appl. No. 14/246,143, 20 pages.
European Patent Office Communication, dated Mar. 3, 2016, regarding Application No. 11714174.7, 5 pages.

* cited by examiner

AUTOMATED POSTFLIGHT TROUBLESHOOTING

BACKGROUND INFORMATION

1. Field

The present disclosure relates to a maintenance system and, in particular, to a method and apparatus for maintenance planning for products. Still more particularly, the present disclosure relates to a computer implemented method, apparatus, and computer usable program code for identifying external maintenance discrepancies.

2. Background

In planning for maintenance of products, a number of different processes may be present. When the product is an aircraft, for example, computer based maintenance planning tools may aid in the planning process by integrating regulatory requirements with emerging maintenance needs to help calculate the time required to perform the many tasks necessary to keep the aircraft in airworthy condition and compliant with federal regulations.

Time for conducting post-flight maintenance is lost between the time an aircraft lands and the time the aircraft reaches the ramp from the runway. Increased turn around time due to maintenance requirements is more likely as the maintenance inspection time is lost while an aircraft is taxiing. Visual health inspections are time consuming and human endurance for lengthy, repetitive inspections induces failure rates for detecting anomalies. The human eye is also limited in spectrum and may have difficulty seeing certain types of fluid leaks.

Accordingly, there is a need for a method and apparatus which takes into account one or more of the issues discussed above as well as possibly other issues.

SUMMARY

The advantageous embodiments provide a method and system for identifying anomalies on an object. The advantageous embodiments detect a presence of the object in a control area using a sensor system. In response to detecting the presence of the object in the control area, the object is identified using the sensor system. Scan priorities are identified for the object using the sensor system. The object is scanned while the object is within the control area to form scan results. The scan results are analyzed and a determination is made as to whether a number of maintenance anomalies are detected on the object using the scan results.

The features, functions, and advantages can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the advantageous embodiments are set forth in the appended claims. The advantageous embodiments, however, as well as a preferred mode of use, further objectives and advantages thereof, will best be understood by reference to the following detailed description of an advantageous embodiment of the present disclosure when read in conjunction with the accompanying drawings, wherein:

DETAILED DESCRIPTION

Figure 1:
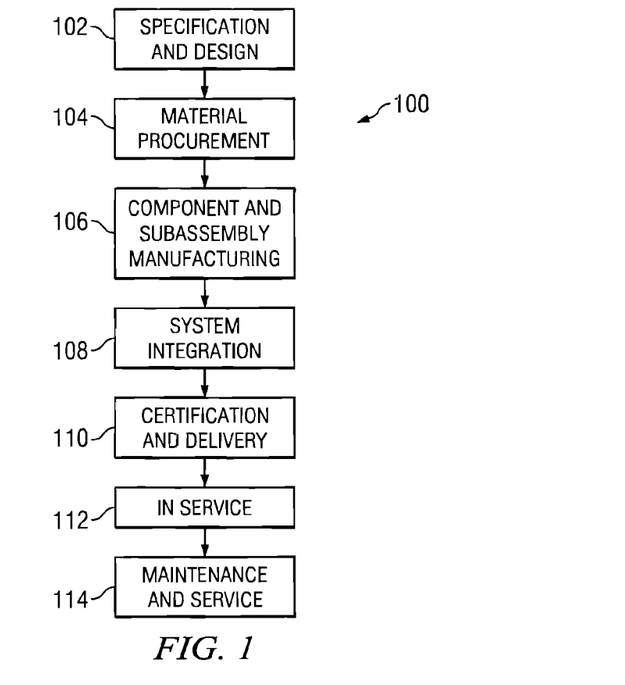
FIG. 1 is a diagram illustrating an aircraft manufacturing and service method in which an advantageous embodiment may be implemented.
Figure 2:
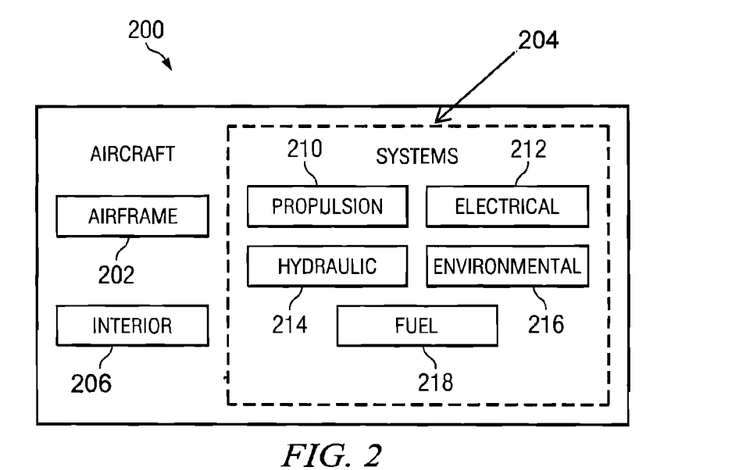
FIG. 2 is a diagram of an aircraft in which an advantageous embodiment may be implemented.

Referring more particularly to the drawings, embodiments of the disclosure may be described in the context of the aircraft manufacturing and service method 100 as shown in FIG. 1 and aircraft 200 as shown in FIG. 2. Turning first to FIG. 1, a diagram illustrating an aircraft manufacturing and service method is depicted in accordance with an advantageous embodiment. During pre-production, aircraft manufacturing and service method 100 may include specification and design 102 of aircraft 200 in FIG. 2 and material procurement 104.

During production, component and subassembly manufacturing 106 and system integration 108 of aircraft 200 in FIG. 2 takes place. Thereafter, aircraft 200 in FIG. 2 may go through certification and delivery 110 in order to be placed in service 112. While in service by a customer, aircraft 200 in FIG. 2 is scheduled for routine maintenance and service 114, which may include modification, reconfiguration, refurbishment, and other maintenance or service.

Each of the processes of aircraft manufacturing and service method 100 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of venders, subcontractors, and suppliers; and an operator may be an airline, leasing company, military entity, service organization, and so on.

With reference now to FIG. 2, a diagram of an aircraft is depicted in which an advantageous embodiment may be implemented. In this example, aircraft 200 is produced by aircraft manufacturing and service method 100 in FIG. 1 and may include airframe 202 with a plurality of systems 204 and interior 206. Examples of systems 204 include one or more of propulsion system 210, electrical system 212, hydraulic system 214, environmental system 216, and fuel 218. Any number of other systems may be included. Although an aerospace example is shown, different advantageous embodiments may be applied to other industries, such as the automotive industry.

Apparatus and methods embodied herein may be employed during any one or more of the stages of aircraft manufacturing and service method 100 in FIG. 1. For example, external maintenance anomalies identified during certification and delivery 110 in FIG. 1 may be addressed while aircraft 200 is in maintenance and service 114 in FIG. 1.

Also, one or more apparatus embodiments, method embodiments, or a combination thereof may be utilized during production stages, such as component and subassembly manufacturing 106 and system integration 108 in FIG. 1, for example, without limitation, by substantially expediting the assembly of or reducing the cost of aircraft 200. Similarly, one or more of apparatus embodiments, method embodiments, or a combination thereof may be utilized while aircraft 200 is in service 112 or during maintenance and service 114 in FIG. 1.

For example, different advantageous embodiments may be employed to identify external maintenance anomalies during component and subassembly manufacturing 106. Advantageous embodiments also may be implemented to identify external maintenance anomalies during system integration 108, certification and delivery 110, in service 112, and/or maintenance and service 114.

The different advantageous embodiments recognize and take into account that currently used systems for conducting post-flight maintenance lose the time from when an aircraft lands until it reaches the ramp from the runway, which increases the potential turn around time due to maintenance requirements that may not be identified until the aircraft has finished taxiing. The different advantageous embodiments recognize that initial maintenance inspection time is lost while an aircraft is taxiing.

The different advantageous embodiments recognize and take into account that currently used systems for identifying external maintenance anomalies for an aircraft, for example, rely upon human inspection at the airport gate or maintenance area. The different advantageous embodiments recognize that the locations at which inspection for external maintenance anomalies can take place is limited. The different advantageous embodiments also recognize that currently used systems may cope with this problem by utilizing maintenance datalinks, which have the ability to detect some structural health issues but lack any ability to autonomously detect latent surface anomalies, such as cracks or dents for example.

The different advantageous embodiments also recognize and take into account that maintenance datalinks are expensive and have bandwidth limitations that significantly restrict the amount of information that can be transmitted. The different advantageous embodiments recognize that this leads to many companies choosing not to use maintenance datalinks at all, and relying solely on inspections that take place after the aircraft has finished taxiing.

Thus, the different advantageous embodiments provide a method, apparatus, and computer program product for identifying anomalies on an object. The advantageous embodiments detect a presence of the object in a control area using a sensor system. In response to detecting the presence of the object in the control area, the object is identified using the sensor system. Scan priorities are identified for the object using the sensor system. The object is scanned as the object moves through the control area to form scan results. The scan results are analyzed and a determination is made as to whether a number of maintenance anomalies are detected on the object using the scan results.

The different advantageous embodiments provide for quicker troubleshooting information for an aircraft anomaly, and regularly occurring, repetitive inspections that may detect anomalies that have indications outside of the human visual spectrum. Maintenance crews can address anomalies more efficiently without lost time for inspection, and focus on conducting the required maintenance.

Figure 3:
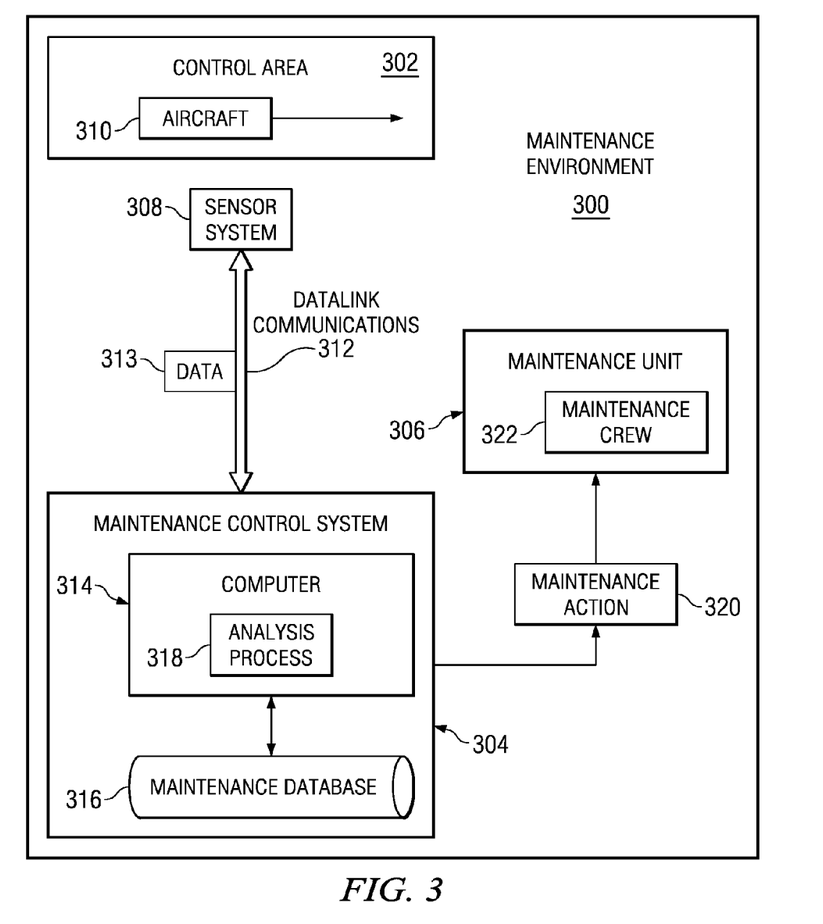
FIG. 3 is a diagram of a maintenance environment in accordance with an advantageous embodiment.

Turning now to FIG. 3, a diagram of a maintenance environment is depicted in accordance with an advantageous embodiment. Maintenance environment 300 may be implemented during aircraft manufacturing and service method 100 as shown in FIG. 1. For example, maintenance environment 300 may be implemented during maintenance and service 114 in FIG. 1.

Maintenance environment 300 includes control area 302, maintenance control system 304, maintenance unit 306, and sensor system 308. Control area 302 is any location and/or area in which an object may be scanned and/or inspected. Control area 302 may be, for example, without limitation, a taxiway, runway, paved surface, and/or any area or location in which an object may be scanned. In an advantageous embodiment, control area 302 is a chokepoint of object traffic moving throughout a larger environment. Control area 302 may include sensor system 308. Aircraft 310 moves through control area 302 in this example.

Sensor system 308 may be implemented as a number of sensor systems within and/or adjacent to control area 302. As used herein, a number refers to one or more sensor systems. Sensor system 308 may be distributed on a number of sides of control area 302. For example, in an advantageous embodiment, sensor system 308 may be distributed on either side of a runway or a taxiway. In another advantageous embodiment, sensor system 308 may be distributed at either end of a runway or a taxiway.

Aircraft 310 is an example of an object moving through control area 302. Aircraft 310 may be one example of aircraft 200 in FIG. 2. Sensor system 308 scans aircraft 310 as aircraft 310 moves through control area 302. Sensor system 308 may detect anomalies on aircraft 310, such as, without limitation, cracks, dents, depressions, bulges, buckling, warping, drips, leaks, corrosion, rust, open/missing access panels, and/or other anomalies.

Sensor system 308 communicates with maintenance control system 304 using datalink communications 312. Datalink communications 312 may use a medium that is, for example without limitation, physical and/or wireless. Datalink communications 312 also may be part of a network. Sensor system 308 may transmit scan results in the form of data 313 over datalink communications 312 to maintenance control system 304.

In this illustrative example, maintenance control system 304 includes computer 314 and maintenance database 316. Computer 314 may be any type of data processing system. Computer 314 includes analysis process 318. Analysis process 318 interacts with maintenance database 316 to identify maintenance anomalies using scan results from sensor system 308. Analysis process 318 may generate maintenance action 320 and transmit maintenance action 320 to maintenance unit 306. Maintenance action 320 may be, for example, a repair, an adjustment, a replacement of a part, no action required, and/or some other suitable action. Maintenance crew 322 of maintenance unit 306 may receive maintenance action 320 from analysis process 318 and execute maintenance action 320 on aircraft 310.

The illustration of maintenance environment 300 in FIG. 3 is not meant to imply physical or architectural limitations on the manner in which different advantageous embodiments may be implemented. Other components in addition or in place of the ones illustrated may be used. Some components may be unnecessary in some advantageous embodiments. Also, the blocks are presented to illustrate some functional components and combined and/or divided into different blocks when implemented in hardware and/or software.

For example, in some advantageous embodiments, analysis process 318 could be implemented within sensor system 308. Also, maintenance database 316 may be located at the same data processing system or distributed over many data processing systems. As another example, additional sensor systems in addition to sensor system 308 maybe used in control area 302 to scan other aircraft in addition to aircraft 310. Also, maintenance environment 300 also may have additional control areas in addition to control area 302. In other advantageous embodiments, data 313 transmitted by sensor system 308 over datalink communications 312 may pass through intermediate nodes before being received by maintenance control system 304.

Figure 4:
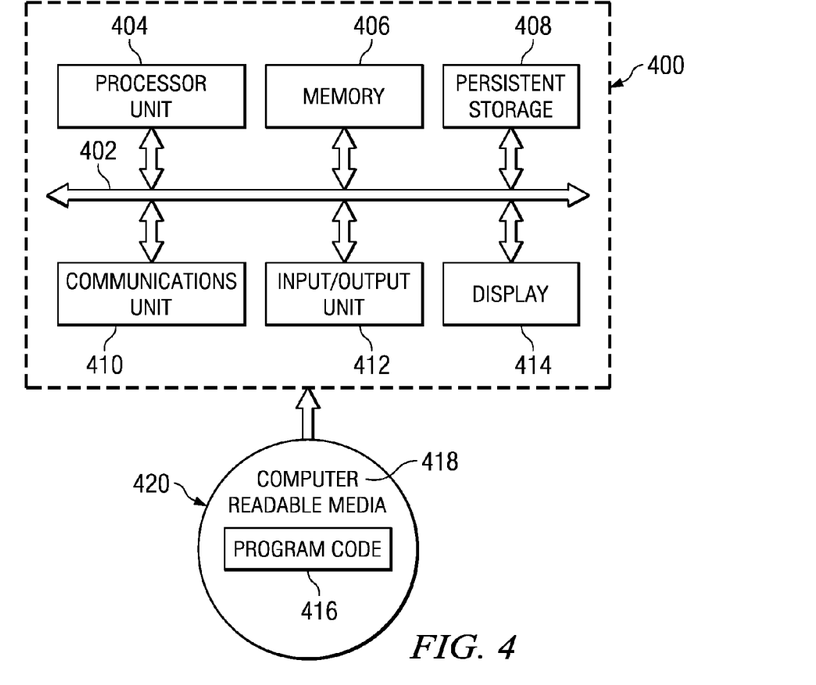
FIG. 4 is a diagram of a data processing system in accordance with an advantageous embodiment.

With reference now to FIG. 4, a diagram of a data processing environment is provided in which advantageous embodiments may be implemented. It should be appreciated that FIG. 4 is only an example and is not intended to assert or imply any limitation with regard to the environments in which different embodiments may be implemented. Many modifications to the depicted environment may be made.

FIG. 4 depicts a diagram of a data processing system in accordance with an advantageous embodiment. Data processing system 400 may be used to implement various computers and/or devices used in the different advantageous embodiments. Network data processing system 400 may be used during aircraft maintenance and service method 114 in FIG. 1. For example, data processing system 400 may be used to implement the advantageous embodiments during various steps and/or phases of aircraft maintenance and service method 114.

In this illustrative example, data processing system 400 includes communications fabric 402, which provides communications between processor unit 404, memory 406, persistent storage 408, communications unit 410, input/output (I/O) unit 412, and display 414.

Processor unit 404 serves to execute instructions for software that may be loaded into memory 406. Processor unit 404 may be a number of one or more processors or may be a multi-processor core, depending on the particular implementation. Further, processor unit 404 may be implemented using one or more heterogeneous processor systems in which a main processor is present with secondary processors on a single chip. As another illustrative example, processor unit 404 may be a symmetric multi-processor system containing multiple processors of the same type.

Memory 406 and persistent storage 408 are examples of storage devices. A storage device is any piece of hardware that is capable of storing information either on a temporary basis and/or a permanent basis. Memory 406, in these examples, may be, for example, a random access memory or any other suitable volatile or non-volatile storage device.

A storage device, as used herein, is hardware that is capable of storing computer program code in the functional form and/or data. Persistent storage 408 may take various forms depending on the particular implementation. For example, persistent storage 408 may contain one or more components or devices. For example, persistent storage 408 may be a hard drive, a flash memory, a rewritable optical disk, a rewritable magnetic tape, or some combination of the above. The media used by persistent storage 408 also may be removable. For example, a removable hard drive may be used for persistent storage 408.

Communications unit 410, in these examples, provides for communications with other data processing systems or devices. In these examples, communications unit 410 is a network interface card. Communications unit 410 may provide communications through the use of either or both physical and wireless communications links.

Input/output unit 412 allows for input and output of data with other devices that may be connected to data processing system 400. For example, input/output unit 412 may provide a connection for user input through a keyboard and mouse. Further, input/output unit 412 may send output to a printer. Display 414 provides a mechanism to display information to a user.

Instructions for the operating system and applications or programs are located on persistent storage 408. These instructions may be loaded into memory 406 for execution by processor unit 404. The processes of the different embodiments may be performed by processor unit 404 using computer implemented instructions, which may be located in a memory, such as memory 406. These instructions are referred to as program code, computer usable program code, or computer readable program code that may be read and executed by a processor in processor unit 404. The program code in the different embodiments may be embodied on different physical or tangible computer readable media, such as memory 406 or persistent storage 408.

Program code 416 is located in a functional form on computer readable media 418 that is selectively removable and may be loaded onto or transferred to data processing system 400 for execution by processor unit 404. Program code 416 and computer readable media 418 form computer program product 420 in these examples. In one example, computer readable media 418 may be in a tangible form, such as, for example, an optical or magnetic disc that is inserted or placed into a drive or other device that is part of persistent storage 408 for transfer onto a storage device, such as a hard drive that is part of persistent storage 408. In a tangible form, computer readable media 418 also may take the form of a persistent storage, such as a hard drive, a thumb drive, or a flash memory that is connected to data processing system 400. The tangible form of computer readable media 418 is also referred to as computer recordable storage media. In some instances, computer readable media 418 may not be removable.

Alternatively, program code 416 may be transferred to data processing system 400 from computer readable media 418 through a communications link to communications unit 410 and/or through a connection to input/output unit 412. The communications link and/or the connection may be physical or wireless in the illustrative examples. The computer readable media also may take the form of non-tangible media, such as communications links or wireless transmissions containing the program code.

In some advantageous embodiments, program code 416 may be downloaded over a network to persistent storage 408 from another device or data processing system for use within data processing system 400. For instance, program code stored in a computer readable storage medium in a server data processing system may be downloaded over a network from the server to data processing system 400. The data processing system providing program code 416 may be a server computer, a client computer, or some other device capable of storing and transmitting program code 416.

The different components illustrated for data processing system 400 are not meant to provide architectural limitations to the manner in which different embodiments may be implemented. The different advantageous embodiments may be implemented in a data processing system including components in addition to or in place of those illustrated for data processing system 400. Other components shown in FIG. 4 can be varied from the illustrative examples shown. The different embodiments may be implemented using any hardware device or system capable of executing program code. As one example, the data processing system may include organic components integrated with inorganic components and/or may be comprised entirely of organic components excluding a human being. For example, a storage device may be comprised of an organic semiconductor.

As another example, a storage device in data processing system 400 is any hardware apparatus that may store data. Memory 406, persistent storage 408 and computer readable media 418 are examples of storage devices in a tangible form.

In another example, a bus system may be used to implement communications fabric 402 and may be comprised of one or more buses, such as a system bus or an input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. Further, a memory may be, for example, memory 406 or a cache such as found in an interface and memory controller hub that may be present in communications fabric 402.

Figure 5:
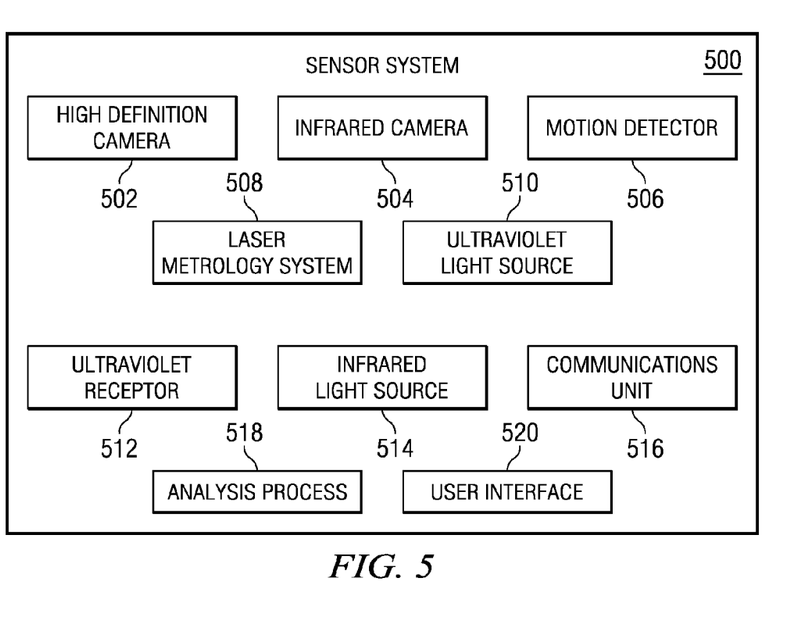
FIG. 5 is a diagram of a sensor system in accordance with an advantageous embodiment.

With reference now to FIG. 5, a diagram of a sensor system is depicted in accordance with an advantageous embodiment. Sensor system 500 may be used with or implemented as part of a data processing system, such as data processing system 400 in FIG. 4. Sensor system 500 is an example of one implementation of sensor system 308 in FIG. 3.

Sensor system 500 is a system with a number of sensors and may be a number of sensor systems used to collect information about an object moving through an environment. A number as used herein refers to one or more items. For example, a number of sensors is one or more sensors, and a number of sensor systems is one or more sensor systems.

In one advantageous embodiment, sensor system 500 includes high definition camera 502, infrared camera 504, motion detector 506, laser metrology system 508, ultraviolet light source 510, ultraviolet receptor 512, infrared sensor 514, communications unit 516, analysis process 518, and user interface 520.

High definition camera 502 may be a standard still-image camera, which may be used alone for color information or with a second camera to generate stereoscopic, or three-dimensional, images. Infrared camera 504 may form an image using infrared radiation. When high definition camera 502 is used along with a second camera to generate stereoscopic images, the cameras may be set with different exposure settings to provide improved performance over a range of lighting conditions. High definition camera 502 may also be a video camera that captures and records moving images.

Motion detector 506 is any device that contains a physical mechanism or electronic sensor that is capable of detecting motion. Motion detector 506 may detect the presence of a moving object within a control area, such as control area 302 in FIG. 3. In one advantageous embodiment, motion detector 506 may be integrated with or connected to other components of sensor system 500 in order to activate other components, such as high definition camera 502 and infrared camera 504 for example, to the presence of a moving object within the field of view. In another advantageous embodiment, motion detector 506 may be configured to send a signal to analysis process 518 when the presence of a moving object is detected.

Laser metrology system 508 is any scanning laser metrology system that uses laser beams to measure a surface. Laser metrology system 508 scans a surface and creates a three-dimensional map, which can be used to measure anomalies, such as, for example, without limitation, cracks, dents, and the like. Laser metrology system 508 may be configured to measure a surface, such as aircraft 310 in FIG. 3 moving through control area 302 for example.

Ultraviolet light source 510 emits ultraviolet light. Ultraviolet light is electromagnetic radiation with a wavelength shorter than that of visible light. Ultraviolet light may be used to detect anomalies such as, for example, fluid leaks that are difficult to identify in a visible light spectrum. Ultraviolet receptor 512 receives the bounce-back of ultraviolet light wavelengths when ultraviolet light source 510 emits ultraviolet light. Ultraviolet receptor 512 transforms the bounce-back wavelengths into a visible light spectrum viewable by a human eye. One advantageous embodiment of ultraviolet receptor 512 may be a digital camera using ultraviolet light filters. This digital camera may capture images of an object illuminated by ultraviolet light source 510 in an ultraviolet light range.

Infrared sensor 514 detects differences in ambient temperature. Infrared sensor 514 may be used to detect anomalies such as, for example, fluid leaks that are difficult to identify in a visible light spectrum. Infrared sensor 514 is capable of detecting fluid leaks or streaks because the fluid may be a different temperature than the immediate surrounding surface of the object. The difference in temperature may reveal the fluid as a different temperature gradient shade in the infrared scan. In another advantageous embodiment, infrared scans may show hot spots on the surface of an object that should not normally be there as compared to an as designed infrared scan of the object. These hot spots can be indicative of anomalies on or below the surface of the object. For example, a hot spot below a mid-wing surface of an aircraft that corresponds to the position of a fuel pump beneath the wing surface may be indicative of the fuel pump overheating and/or being on the verge of failure.

Communications unit 516, in these examples, provides for communications with other data processing systems or devices. In one advantageous embodiment, communications unit 310 may be a network interface card. Communications unit 310 may provide communications through the use of either or both physical and wireless communications links.

In an advantageous embodiment, sensor system 500 detects an object and sends information about the object to analysis process 518. Analysis process 518 identifies the object detected by motion detector 506 and analyzes the data obtained by components of sensor system 500 such as, for example, images from high definition camera 502 and infrared camera 504, measurements from laser metrology system 508, wavelengths from ultraviolet light source 510 and temperature differences detected by infrared sensor 514. Analysis process 518 may also identify whether or not the object detected is to be scanned by the different components of sensor system 500, scan priorities, if any, that exist for the object, and maintenance discrepancies found for the object.

User interface 520 allows for the input of data into sensor system 500 and/or analysis process 518, as well as displaying output from sensor system 500 and/or analysis process 518. User interface 520 may be, in one advantageous embodiment, presented on a display monitor, such as display 414 in FIG. 4.

In an advantageous embodiment, sensor system 500 may include a number of redundant sensors. As used herein, a number refers to one or more sensors. A number of sensors may be a heterogeneous and/or homogeneous number of sensors. Redundant sensors in these examples are sensors that may be used to compensate for the loss and/or inability of other sensors to obtain information needed to perform a scan of an object, such as an aircraft, for example. A redundant use of the number of sensors is governed by the intended use of each of the sensors and their degradation in certain dynamic conditions. For example, dynamic conditions may be terrestrial and weather conditions that affect sensors and their ability to contribute to an accurate scan of an object. Such conditions may include, without limitation, sun, clouds, artificial illumination, full moon light, new moon darkness, degree of sun brightness based on sun position due to season, shadows, fog, smoke, sand, dust, rain, snow, and the like.

The illustration of sensor system 500 in FIG. 5 is not meant to imply physical or architectural limitations on the manner in which different advantageous embodiments may be implemented. Other components in addition or in place of the ones illustrated may be used. Some components may be unnecessary in some advantageous embodiments. For example, in some advantageous embodiments, analysis process 518 could be located remotely from sensor system 500 and accessed using communications unit 516.

Also, the blocks are presented to illustrate some functional components and combined and/or divided into different blocks when implemented in hardware and/or software. For example, in some advantageous embodiments, analysis process 518 could be integrated with communications unit 516.

Figure 6:
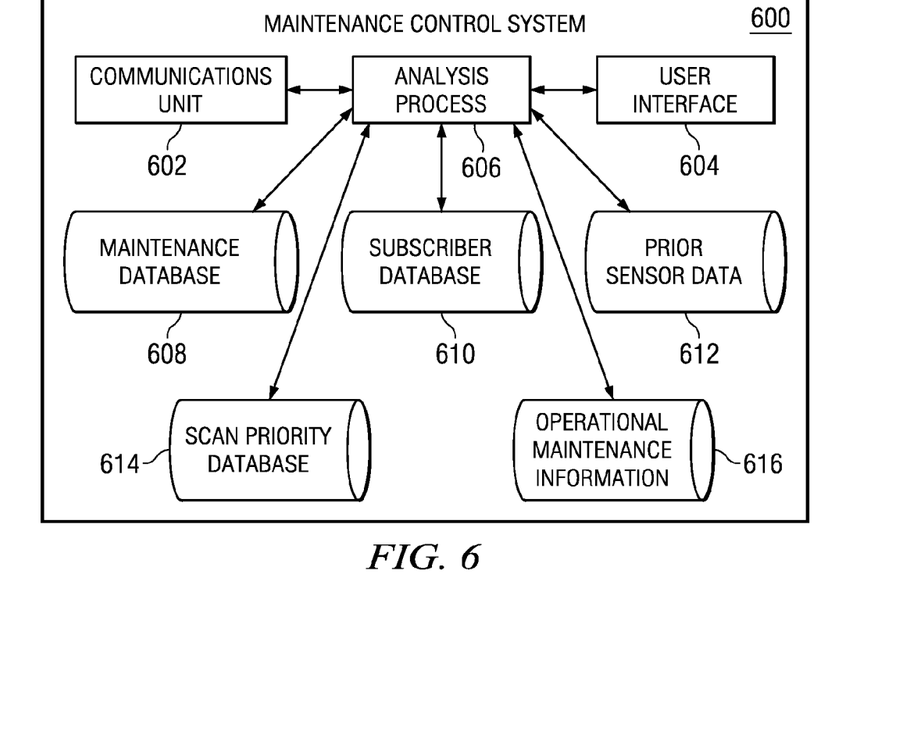
FIG. 6 is a diagram of a maintenance control system in accordance with an advantageous embodiment.

With reference now to FIG. 6, a diagram of a maintenance control system is depicted in accordance with an advantageous embodiment. Maintenance control system 600 may be implemented in a data processing system, such as data processing system 400 in FIG. 4. Maintenance control system 600 is an example of one implementation of maintenance control system 304 in FIG. 3.

Maintenance control system 600 includes communications unit 602, user interface 604, analysis process 606, maintenance database 608, subscriber database 610, prior sensor data 612, scan priority database 614, and operational maintenance information 616.

Communications unit 602, in these examples, provides for communications with other data processing systems or devices, such as sensor system 500 in FIG. 5 for example. In one advantageous embodiment, communications unit 310 may be a network interface card. Communications unit 310 may provide communications through the use of either or both physical and wireless communications links.

User interface 604 allows for the input of data into maintenance control system 600 and/or analysis process 606, as well as displaying output from maintenance control system 600 and/or analysis process 606. User interface 604 may be, in one advantageous embodiment, presented on a display monitor, such as display 414 in FIG. 4. In another advantageous embodiment, user interface 604 may also include peripherals such as, for example, a keyboard and mouse configured to interact with a monitor integrated with display 414 in FIG. 4.

In an advantageous embodiment, sensor system 500 in FIG. 5 detects an object and sends information about the object to analysis process 606. Analysis process 606 identifies the object detected by motion detector 506 in FIG. 5 and analyzes the data obtained by components of sensor system 500 in FIG. 5. Analysis process 606 may also identify whether or not the object detected is to be scanned by a sensor system, such as sensor system 500 in FIG. 5, scan priorities, if any, that exist for the object, and maintenance discrepancies found for the object.

Maintenance database 608 contains maintenance planning data for a number of different models of an object as well as maintenance information for specific objects. For example, in one advantageous embodiment, maintenance database 608 contains maintenance planning data for a number of different models of an aircraft as well as maintenance information for a number of specific aircraft. In one advantageous embodiment, maintenance database 608 is a fleet-wide database used for tracking maintenance of aircraft at the macro and micro levels. This maintenance planning data describes what preventative maintenance must be performed to maintain airworthiness and federal compliance for a given aircraft. This information may include regulatory requirements and service bulletins.

Subscriber database 610 contains information about the customers that have subscribed to the service for scanning an object and identifying external anomalies. In one advantageous embodiment, subscriber database 610 may identify the tail numbers of aircraft that are owned by subscribers. Analysis process 606 may interact with subscriber database 610 to determine whether or not an object detected by a sensor system, such as sensor system 500 in FIG. 5, is an object that is a subscriber of the scanning service. If an object is not found within subscriber database 610, analysis process 606 may direct the sensor system not to perform a scan of the object. In another advantageous embodiment, analysis process 606 may receive the scan results, but may prevent the results from being processed if the object is not found within subscriber database 610.

Prior sensor data 612 contains information about prior scans of the object that is detected by a sensor system. Prior sensor data 612 may be used to detect reoccurring anomalies, or for trend monitoring for a particular object or type of object.

Scan priority database 614 contains a hierarchy of anomaly priorities for a sensor system to address. In an advantageous embodiment, scan priority database 614 may rank sections of an object, or particular anomalies that are to be sought out during a scan in order of priority. Priority may depend, in part, upon information obtained from operational maintenance information 616. In an advantageous embodiment, scan priorities are based on datalink transmissions received in-flight from an aircraft, and maintenance anomalies identified from the datalink transmission are given first tier priority to scan after flight.

Operational maintenance information 616 contains maintenance information transmitted during operation of an object. In an advantageous embodiment, operational maintenance information 616 may be maintenance information transmitted during flight of an aircraft, such as potential stress due to a hard landing or severe storm in-flight, for example. Operational maintenance information 616 may be transmitted via a datalink, such as the Aircraft Communications Addressing and Reporting System (ACARS) for example.

Analysis process 606 interacts with maintenance database 608, subscriber database 610, prior sensor data 612, scan priority database 614, and operational maintenance information 616 to identify potential maintenance needs for an object and assign scan priorities to a sensor system, such as sensor system 500 in FIG. 5.

The illustration of maintenance control system 600 in FIG. 6 is not meant to imply physical or architectural limitations on the manner in which different advantageous embodiments may be implemented. Other components in addition or in place of the ones illustrated may be used. Some components may be unnecessary in some advantageous embodiments. For example, in some advantageous embodiments, analysis process 606 could be located remotely from maintenance control system, for example integrated in sensor system 500 in FIG. 5, and access databases within maintenance control system 600 using communications unit 602. Also, the blocks are presented to illustrate some functional components and combined and/or divided into different blocks when implemented in hardware and/or software. For example, in some advantageous embodiments, maintenance database 608, subscriber database 610, prior sensor data 612, scan priority database 614, and operational maintenance information 616 may be located in a storage device, such as persistent storage 408 in FIG. 4, or distributed over many data processing systems. As another example, in some advantageous embodiments, scan priority database 614 may prioritize anomaly tiers without additional operational maintenance information.

Figure 7:
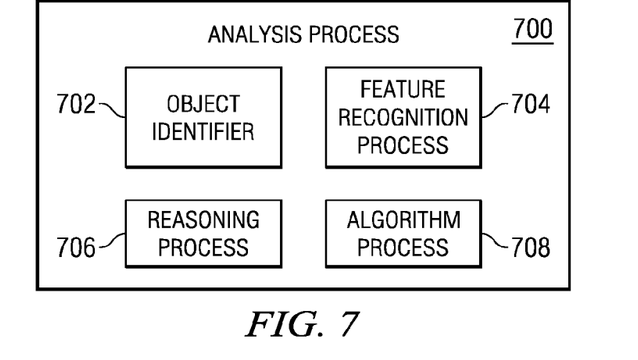
FIG. 7 is a diagram of an analysis process in accordance with an advantageous embodiment.

With reference now to FIG. 7, a diagram of an analysis process is depicted in accordance with an advantageous embodiment. Analysis process 700 may be implemented in a data processing system, such as data processing system 400 in FIG. 4. Analysis process 700 is an example of one implementation of analysis process 318 in FIG. 3.

Analysis process 700 includes object identifier 702, feature recognition process 704, reasoning process 706, and algorithm process 708. Object identifier 702 receives input from a sensor system, such as sensor system 500 in FIG. 5, when an object is detected. Object identifier 702 uses the information received, such as an image from a high definition camera, to detect an identifier of the object. For example, in an advantageous embodiment, a tail number of an aircraft may be an identifier detected from an image captured by a high definition camera. Object identifier 702 interacts with a subscriber database, such as subscriber database 610 in FIG. 6, to determine whether information about the object received from a sensor system should be processed, or whether a scan of the object by a sensor system should take place.

Feature recognition process 704 processes the information received from a sensor system and identifies what the information depicts. For example, if an ultraviolet light source and receptor detects a substance flowing from a surface, feature recognition process 704 identifies the substance as a fluid and the surface as the wing. In an illustrative example, a substance such as hydraulic fluid will illuminate when a specific wavelength of ultraviolet light shines on the surface of the hydraulic fluid. A sensor system, such as sensor system 500 in FIG. 5, may contain an ultraviolet light source and receptor, such as ultraviolet light source 510 and ultraviolet receptor 512 in FIG. 5. When an aircraft passes by the sensor system, ultraviolet light source 510 will shine light on the surface of the aircraft and ultraviolet receptor 512 will be programmed to detect the expected glow of the hydraulic fluid. Feature recognition process 704 recognizes the feature of a hydraulic fluid leak if illumination is detected by the sensor system. If no illumination is detected, analysis process 700 determines that there is no leak at the area of the surface scanned, such as a servicing point, for example. A servicing point may be, for example, refueling ports, single point refueling ports, wing refueling ports, hydraulic servicing ports, pneumatic servicing ports, and/or some other suitable servicing points.

Reasoning process 706 tags anomalies, or gripes, and keeps records of how anomalies are resolved. In an advantageous embodiment, over time, reasoning process 706 learns how particular anomalies are resolved and may diagnose anomalies detected. User input may be used to aid reasoning process 706 in learning how to correctly diagnose anomalies for future anomaly diagnosis. For example, in an advantageous embodiment, using the illustrative example of the hydraulic fluid leak above, in the absence of detected illumination, reasoning process 706 would determine that there is no leak. If illumination is detected, reasoning process 706 may send a command to the sensor system, such as sensor system 500 in FIG. 5, to capture an image for display to the maintenance crew, such as maintenance crew 322 in FIG. 3. The image may be captured using a camera, such as high definition camera 502 in FIG. 5, for example. Reasoning process 706 may then determine that the illumination detected is a streak of fluid coming from a servicing point, for example, which may be an indication of a persistent leak. Reasoning process 706 may determine the amount of fluid present at the servicing point, and further determine that a small ring of fluid is residual fluid remaining from the last time hydraulic fluid was added to the reservoir, while a large streak of fluid is more indicative of a leak.

Reasoning process 706 determines the anomalies or anomalies present in order to generate a maintenance order. Reasoning process 706 receives user input as to how a number of anomalies are resolved and over time learns how specific anomalies are resolved, which allows reasoning process 706 to provide anomaly resolution diagnosis during subsequent processes.

Algorithm process 708 includes specific sets of instructions used by analysis process 700 to detect anomalies on an object. In one advantageous embodiment, algorithm process 708 uses algorithms that compare the data from the current scan of the object to known "as designed" data for the object. As designed data may be, for example, specific model data for an object. If the current scan of the object differs past a certain threshold from the "as designed" data for the object, algorithm process 708 will flag where the results are different as a possible anomaly. In another advantageous embodiment, algorithm process 708 uses algorithms that recognize certain patterns or shapes, and then compares the current scan of the object to the expected geometry of the object for the location of the object being scanned. For example, if the current scan is of a wing of an aircraft, algorithm process 708 may compare the current scan to the expected geometry for a wing location of the specific model and type of aircraft being scanned. If the shape of the location of the object in the current scan does not exist in the "as designed" data for the object, the shape at that location of the object will be flagged as a possible anomaly. For example, detecting an indention, such as a dent or hole, in what should be a flat area according to the as designed data would be a possible anomaly.

In an advantageous embodiment, reasoning process 706 takes the information processed by algorithm process 708 identifying an anomaly, such as a dent, for example, and recommends action in the form of a maintenance order to address the anomaly. Reasoning process 706 may process current anomalies detected by algorithm process 708 against reasoning process 706 knowledge of past anomalies and the actions taken to address past anomalies in order to determine the corrective action recommended in a maintenance order, for example.

The illustration of analysis process 700 in FIG. 7 is not meant to imply physical or architectural limitations on the manner in which different advantageous embodiments may be implemented. Other components in addition or in place of the ones illustrated may be used. Some components may be unnecessary in some advantageous embodiments. For example, in some advantageous embodiments, algorithm process 708 may contain additional algorithms or different algorithms than the algorithms mentioned above for illustrative purposes. Also, the blocks are presented to illustrate some functional components and combined and/or divided into different blocks when implemented in hardware and/or software. For example, in some advantageous embodiments, reasoning process 706 and algorithm process 708 may be integrated as one process.

Figure 8:
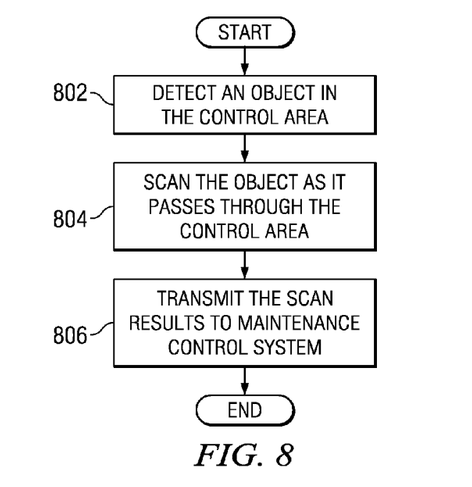
FIG. 8 is a flowchart illustrating a process for scanning an object in accordance with an advantageous embodiment.

With reference now to FIG. 8, a flowchart illustrating a process for scanning an object is depicted in accordance with an advantageous embodiment. The process in FIG. 8 may be implemented in a component such as, for example, sensor system 500 in FIG. 5.

The process begins by detecting an object in a control area (operation 802). The object may be, for example, an aircraft, such as aircraft 310 in FIG. 3, passing through a control area, such as control area 302 in FIG. 3. The object may be detected by a motion detector, such as motion detector 506 in FIG. 5. The process scans the object as it passes through the control area (operation 804). The process then transmits the scan results to a maintenance control system (operation 806), with the process terminating thereafter.

Figure 9:
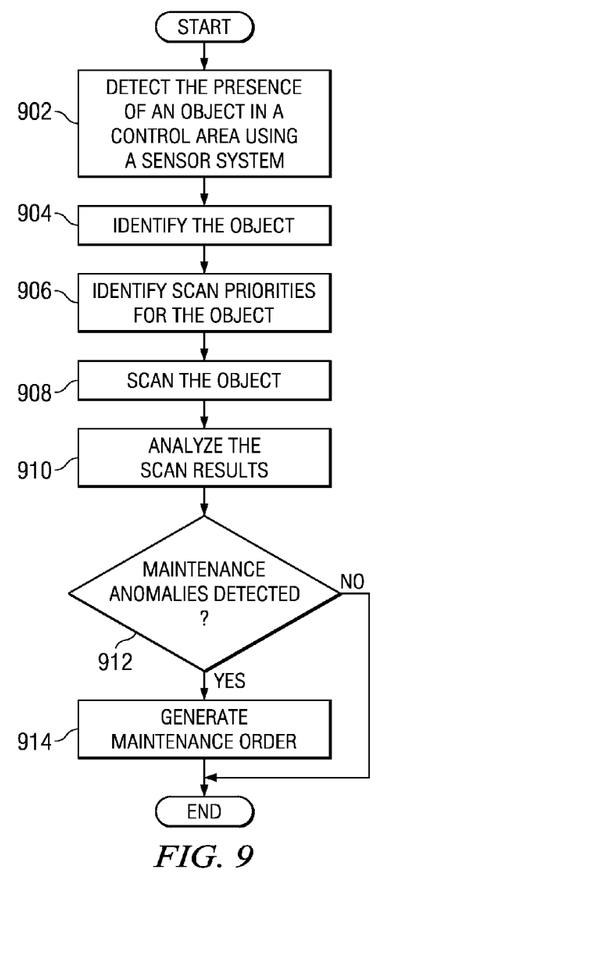
FIG. 9 is a flowchart illustrating a process for identifying maintenance anomalies in accordance with an advantageous embodiment.

With reference now to FIG. 9, a flowchart illustrating a process for identifying maintenance anomalies is depicted in accordance with an advantageous embodiment. The process in FIG. 9 may be implemented in a component such as, for example, sensor system 500 in FIG. 5.

The process begins by detecting an object in a control area (operation 902). The object may be, for example, an aircraft, such as aircraft 310 in FIG. 3, moving through a control area, such as control area 302 in FIG. 3. The object may be detected by a motion detector, such as motion detector 506 in FIG. 5. The process identifies the object (operation 904) using an object identifier, such as object identifier 702 in analysis process 700 of FIG. 7. The process then identifies scan priorities for the aircraft (operation 906) using an analysis process, such as analysis process 518 in FIG. 5.

Next, the process scans the object (operation 908) and analyzes the scan results (operation 910) using an analysis process, such as analysis process 518 in FIG. 5. Then the process determines whether maintenance anomalies are detected (operation 912). If no maintenance anomalies are detected, the process terminates.

If maintenance anomalies are detected, the process generates a maintenance order (operation 914), with the process terminating thereafter.

Figure 10:
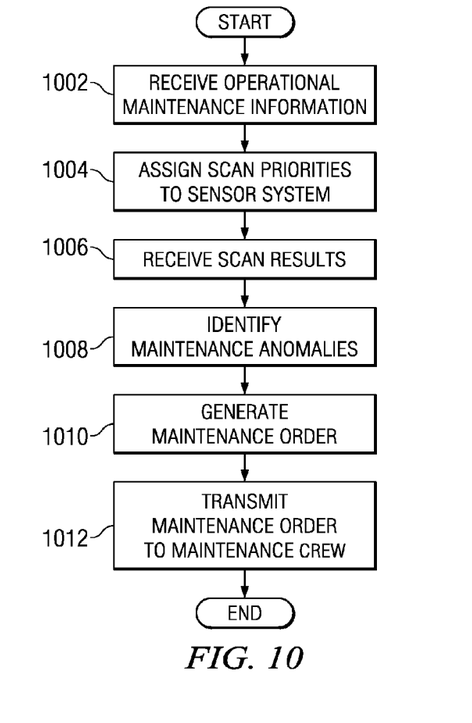
FIG. 10 is a flowchart illustrating a process for identifying maintenance anomalies in accordance with an advantageous embodiment.

With reference now to FIG. 10, a flowchart illustrating a process for generating a maintenance order is depicted in accordance with an advantageous embodiment. The process in FIG. 10 may be implemented in a component such as, for example, maintenance control system 600 in FIG. 6.

The process begins by receiving operational maintenance information (operation 1002). Operational maintenance information may be received from an in-flight datalink of an aircraft, for example. The process assigns scan priorities to a sensor system (operation 1004), such as sensor system 500 in FIG. 5. Scan priorities may be assigned using a scan priority database, such as scan priority database 614 in FIG. 6, or by analysis process 700 in FIG. 7.

The process then receives scan results (operation 1006) from the sensor system. The process identifies maintenance anomalies (operation 1008) and generates a maintenance order (operation 1010). The process then transmits the maintenance order to a maintenance crew (operation 1012), such as maintenance crew 322 in FIG. 3, with the process terminating thereafter.

Figure 11:
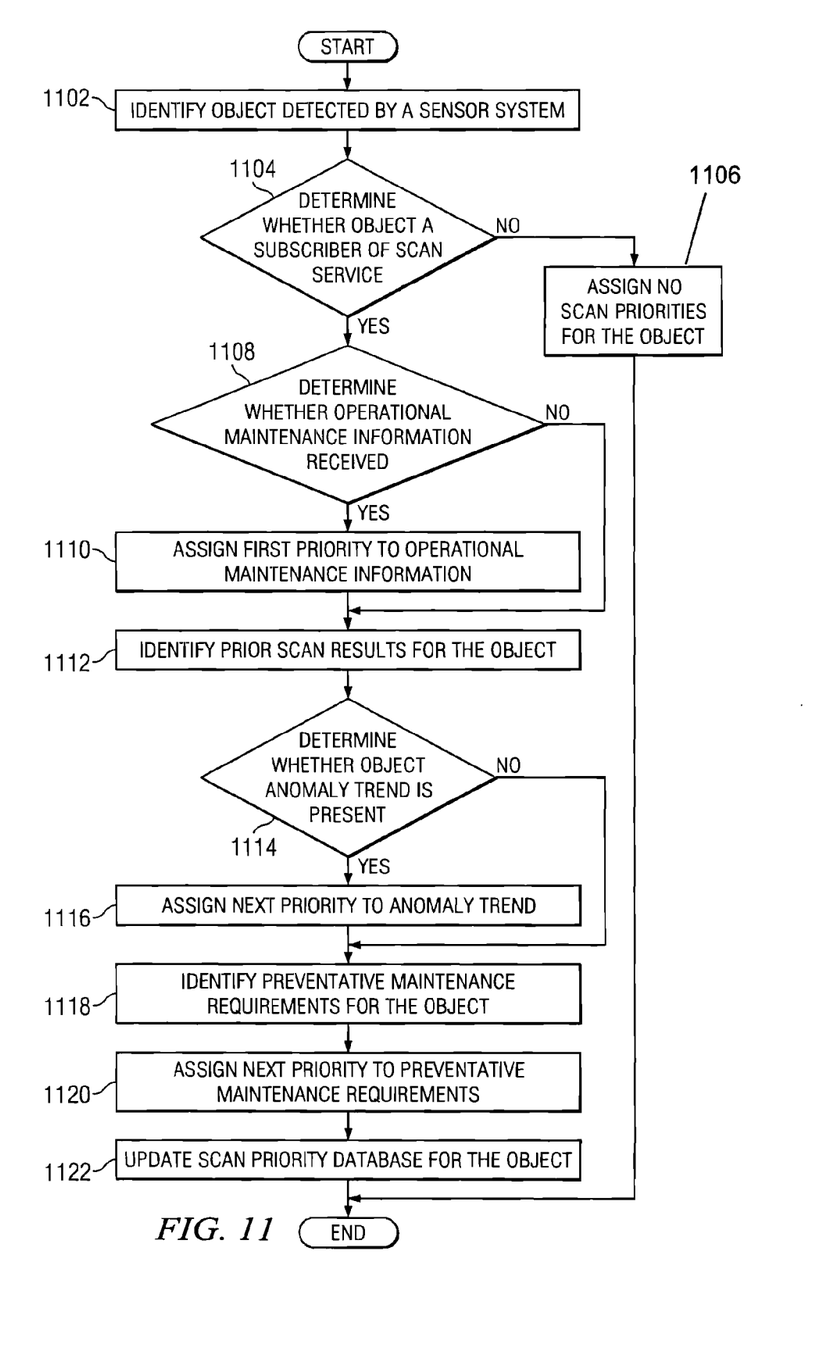
FIG. 11 is a flowchart illustrating a process for identifying maintenance anomalies in accordance with an advantageous embodiment.

With reference now to FIG. 11, a flowchart illustrating a process for identifying scan priorities for an object is depicted in accordance with an advantageous embodiment. The process in FIG. 11 may be implemented in a component such as analysis process 700 in FIG. 7.

The process begins by identifying an object detected by a sensor system (operation 1102). The process may identify an object detected using an object identifier, such as object identifier 702 in FIG. 7. The process determines whether or not the object is a subscriber of the scan service provided by the sensor system (operation 1104), such as sensor system 308 in FIG. 3. The process may determine whether an object is a subscriber using a subscriber database, such as subscriber database 610 in FIG. 6. If the object is not a subscriber, the process assigns no scan priorities for the object (operation 1106) and the process then terminates.

If the object is a subscriber, the process determines whether or not operational maintenance information has been received for the object (operation 1108). The process may determine whether operational maintenance information has been received for an object using a database such as operational maintenance information 616 in FIG. 6. If operational maintenance information has been received for the object, the process assigns first priority to the operational maintenance information (operation 1110), and then identifies prior scan results for the object (operation 1112). If operational maintenance information has not been received for the object, the process proceeds directly to operation 1112.

Next, the process determines whether an anomaly trend is present for the object (operation 1114) based on any prior scan results that may have been identified for the object. Prior scan results for an object may be stored in a database, such as prior sensor data 612 in FIG. 6, if the object has been previously scanned by the sensor system. If an anomaly trend is present, the process assigns next priority to the anomaly trend (operation 1116). Next priority refers to the next level of priority that has yet to be assigned for the current scan priorities being created for the object. As used herein, next may refer to top, middle, bottom, first, second, third, and so on, depending upon any previous priorities that are set before determining whether an anomaly trend is present. For example, if the process previously assigned first priority to operational maintenance information, then next priority for anomaly trends would be second priority. In another illustrative example, if the process previously determined that no operational maintenance information had been received for the object in operation 1108, then next priority for anomaly trends may refer to first priority. The process then identifies preventative maintenance requirements for the object (operation 1118). If the process determines that no anomaly trend is present, the process proceeds directly to operation 1118.

The process assigns next priority to preventative maintenance requirements (operation 1120). The process then updates the scan priority database for the object (operation 1122), with the process terminating thereafter.

The different advantageous embodiments can take the form of an entirely hardware embodiment, an entirely software embodiment, or an embodiment containing both hardware and software elements. Some embodiments are implemented in software, which includes but is not limited to forms, such as, for example, firmware, resident software, and microcode.

Furthermore, the different embodiments can take the form of a computer program product accessible from a computer-usable or computer-readable medium providing program code for use by or in connection with a computer or any device or system that executes instructions. For the purposes of this disclosure, a computer-usable or computer readable medium can generally be any tangible apparatus that can contain, store, communicate, propagate, or transport the program for use by or in connection with the instruction execution system, apparatus, or device.

The computer usable or computer readable medium can be, for example, without limitation an electronic, magnetic, optical, electromagnetic, infrared, or semiconductor system, or a propagation medium. Non limiting examples of a computer-readable medium include a semiconductor or solid state memory, magnetic tape, a removable computer diskette, a random access memory (RAM), a read-only memory (ROM), a rigid magnetic disk, and an optical disk. Optical disks may include compact disk-read only memory (CD-ROM), compact disk-read/write (CD-R/W) and DVD.

Further, a computer-usable or computer-readable medium may contain or store a computer readable or usable program code such that when the computer readable or usable program code is executed on a computer, the execution of this computer readable or usable program code causes the computer to transmit another computer readable or usable program code over a communications link. This communications link may use a medium that is, for example without limitation, physical or wireless.

A data processing system suitable for storing and/or executing computer readable or computer usable program code will include one or more processors coupled directly or indirectly to memory elements through a communications fabric, such as a system bus. The memory elements may include local memory employed during actual execution of the program code, bulk storage, and cache memories which provide temporary storage of at least some computer readable or computer usable program code to reduce the number of times code may be retrieved from bulk storage during execution of the code.

Input/output or I/O devices can be coupled to the system either directly or through intervening I/O controllers. These devices may include, for example, without limitation to keyboards, touch screen displays, and pointing devices. Different communications adapters may also be coupled to the system to enable the data processing system to become coupled to other data processing systems or remote printers or storage devices through intervening private or public networks. Non-limiting examples are modems and network adapters are just a few of the currently available types of communications adapters.

The description of the different advantageous embodiments has been presented for purposes of illustration and description, and is not intended to be exhaustive or limited to the embodiments in the form disclosed. Many modifications and variations will be apparent to those of ordinary skill in the art. For example, although the different advantageous embodiments have been described with respect to aircraft, other advantageous embodiments may be applied to other types of objects. For example, without limitation, other advantageous embodiments may be applied to a mobile platform, a stationary platform, a land-based structure, an aquatic-based structure, a space-based structure and/or some other suitable object. More specifically, the different advantageous embodiments may be applied to, for example, without limitation, a submarine, a bus, a personnel carrier, tank, a train, an automobile, a spacecraft, a space station, a satellite, a surface ship, and/or some other suitable object.

Further, different advantageous embodiments may provide different advantages as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method for identifying a priority for selecting scans for detecting an anomaly on an aircraft in motion on the ground, the method comprising:
   detecting a presence of the aircraft in a control area using a sensor system;
   responsive to detecting the presence of the aircraft in the control area, capturing an image of the aircraft with the sensor system and analyzing the image, using an object identification process within an analysis process, to identify the aircraft;
   responsive to identifying the aircraft, determining, based upon a subscriber status of aircraft, whether or not to scan the aircraft;
   identifying scan priorities, for using the sensor system on the aircraft on the ground after a flight via:
      determining whether the analysis process received a datalink communication, identifying the anomaly with a feature of the aircraft, from the aircraft during the flight;
      assigning a first priority to the anomaly identified in the datalink communication, and identifying prioritization of multiple anomalies received in the datalink communication based upon a hierarchy of anomaly priorities within a scan priority database communicating with the analysis process;
      identifying prior scan results for the aircraft;
      determining, using the analysis process and the prior scan results, whether an anomaly trend is present;
      responsive to a determination that the anomaly trend is present, assigning a second priority to the anomaly trend;
      identifying preventative maintenance requirements; and
      assigning a third priority to preventative maintenance requirements;
   determining, using a designated use for each sensor in the sensor system and a potential for degradation of each sensor influenced by dynamic conditions comprising: a cloud coverage, an artificial illumination, a full moon light, a new moon darkness, a degree of sun brightness based on sun position due to season, a shadow, fog, smoke, sand, dust, rain, and snow, a number of redundant sensors in the sensor system used in scanning the aircraft;
   scanning the aircraft while the aircraft is in motion within the control area to form scan results;
   analyzing, based upon the subscriber status of the aircraft, the scan results;
   determining, using the scan results, whether the scan detected a number of maintenance anomalies on the aircraft, the maintenance anomalies comprising: a crack, a dent, a depression, a bulge, a buckling, a warping, a drip, a leak, a fluid streak, corrosion, rust, an open panel, and a missing panel; and
   transmitting a maintenance order to a maintenance crew, and executing the maintenance order.

2. The method of claim 1, further comprising:
   transmitting the scan results to a maintenance control system, wherein the identifying step is performed by the maintenance control system.

3. The method of claim 1, wherein identifying scan priorities for the aircraft further comprises:
   determining whether the aircraft is a subscriber, via the analysis process interacting with a subscriber database.

4. The method of claim 3, further comprising:
   responsive to a determination that the aircraft is not a subscriber, assigning no scan priorities for the aircraft.

5. The method of claim 3, further comprising:
responsive to a determination that the aircraft is a subscriber, determining whether any operational maintenance information has been received for the aircraft.

6. The method of claim 1, wherein the sensor system further comprises a high definition camera configured to generate three dimensional images.

7. The method of claim 1 further comprising determining which of a plurality of scanning operations to employ in scanning the aircraft.

8. A method for identifying a priority for selecting scans for detecting an anomaly on an aircraft in motion on the ground, the method comprising:
  detecting a presence of the aircraft in a control area using a motion detector;
  capturing an image of the aircraft with a sensor system and analyzing the image to identify the aircraft;
  responsive to identifying the aircraft, determining, based upon a subscriber status of the aircraft, whether or not to scan the aircraft;
  receiving, by a maintenance control system from a datalink communication from the aircraft in a flight immediately preceding the aircraft being in motion on the ground, an identification of the anomaly on the aircraft;
  assigning, by the maintenance control system, scan priorities to the sensor system via;
    assigning a first priority to the anomaly transmitted in the datalink communication, and identifying prioritization of multiple anomalies received in the datalink communication based upon a hierarchy of anomaly priorities within a scan priority database communicating with an analysis process within the maintenance control system;
    identifying prior scan results for the aircraft;
    determining whether an anomaly trend is present using the prior scan results; and
  responsive to a determination that the anomaly trend is present, assigning a second priority to the anomaly trend;
    identifying preventative maintenance requirements; and
    assigning a third priority to preventative maintenance requirements;
  subsequent to assigning scan priorities, updating the scan priority database;
  determining, using a designated use for each sensor in the sensor system and a potential for degradation of each sensor influenced by dynamic conditions comprising: a cloud coverage, an artificial illumination, a full moon light, a new moon darkness, a degree of sun brightness based on sun position due to season, a shadow, fog, smoke, sand, dust, rain, and snow, a number of redundant sensors in the sensor system used in scanning the aircraft;
  scanning the aircraft while the aircraft is in motion within the control area to form scan results, via scanning a surface of the aircraft with a laser metrology system, the laser metrology system creating a three dimensional map for measuring anomalies comprising: a crack, a dent, a depression, a bulge, a buckling, a warping, a drip, a leak, a fluid streak, corrosion, rust, an open panel, and a missing panel;
  scanning the surface of the aircraft with an infrared camera for identifying hot spots on the surface and under the surface, and scanning the surface of the aircraft with an ultraviolet receptor for detecting-fluid leaks;
  receiving scan results of the aircraft in motion on the ground from the sensor system;
  identifying the anomaly using the scan results;
  generating a maintenance order comprising a corrective action for the anomaly; and
  transmitting the maintenance order to a maintenance crew, and executing the maintenance order.

9. An apparatus configured to, in operation, identify a priority for a selection of scans that detect a presence of an anomaly on an aircraft in motion on the ground, the apparatus comprising:
  a sensor system; and
  a maintenance control system comprising a computer connected to the sensor system, the computer configured such that in operation the computer executes an analysis process and performs the steps of:
    detecting the presence of the aircraft in motion on the ground in a control area using the sensor system; responsive to detecting the presence of the aircraft in a control area;
    capturing an image of the aircraft with the sensor system and analyzing the image to identify the aircraft;
    responsive to identifying the aircraft, determining, based upon a subscriber status of the aircraft, whether or not to scan the aircraft;
    identifying scan priorities for the aircraft via:
      determining whether the maintenance control system received a datalink communication identifying the anomaly for the aircraft;
      assigning a first priority to the anomaly and identifying prioritization of multiple anomalies received in the datalink communication based upon a hierarchy of anomaly priorities within a scan priority database communicating with the analysis process within the maintenance control system;
      identifying prior scan results for the aircraft;
      determining whether an anomaly trend is present using the prior scan results; and responsive to a determination that the anomaly trend is present, assigning a second priority to the anomaly trend;
      identifying preventative maintenance requirements; and
      assigning a third priority to preventative maintenance requirements;
    determining, using a designated use for each sensor in the sensor system and a potential for degradation of each sensor influenced by dynamic conditions comprising: a cloud coverage, an artificial illumination, a full moon light, a new moon darkness, a degree of sun brightness based on sun position due to season, a shadow, fog, smoke, sand, dust, rain, and snow, a number of redundant sensors in the sensor system used in scanning the aircraft;
    scanning the aircraft, while the aircraft is in motion on the ground within the control area, to form scan results, via the sensor system:
      scanning a surface of the aircraft with a laser metrology system to create a 3 dimensional map of the surface and thus measuring anomalies comprising: a crack, a dent, a depression, a bulge, a buckling, a warping, a drip, a leak, a fluid streak, corrosion, rust, an open panel, and a missing panel,
      scanning the surface of the aircraft with an infrared camera configured for identifying hot spots on the surface and under the surface, and
      scanning the surface of the aircraft with an ultraviolet receptor configured for detecting fluid leaks;

analyzing the scan results;
determining whether the scan results indicate the anomaly on the aircraft; and
transmitting a maintenance order to a maintenance crew, and executing the maintenance order.

10. The apparatus of claim 9, wherein the computer executes the analysis process to perform the step of identifying scan priorities for the aircraft and further executes the analysis process to perform the step of:
determining whether the aircraft is a subscriber, via the analysis process interacting with a subscriber database.

11. The apparatus of claim 10, wherein the computer further executes the analysis process to perform the step of:
responsive to a determination that the aircraft is not a subscriber, assigning no scan priorities for the aircraft.

12. The apparatus of claim 10, wherein the computer further executes the analysis process to perform the step of:
responsive to a determination that the aircraft is a subscriber, determining whether the analysis process received the datalink from the aircraft.

* * * * *